United States Patent [19]

Yamada et al.

[11] Patent Number: 5,746,976

[45] Date of Patent: May 5, 1998

[54] DETACHABLE GAS ANALYZING APPARATUS

[75] Inventors: Shinsaku Yamada; Hideki Ohashi, both of Miyanohigashi-machi; Sumio Shimizu, Ohtsu; Takao Imaki, Miyanohigashi-machi, all of Japan

[73] Assignee: Horiba Ltd., Kyoto, Japan

[21] Appl. No.: 573,004

[22] Filed: Dec. 15, 1995

[30] Foreign Application Priority Data

| Dec. 17, 1994 | [JP] | Japan | 6-333956 |
| Dec. 17, 1994 | [JP] | Japan | 6-333958 |
| Dec. 17, 1994 | [JP] | Japan | 6-333959 |
| Feb. 21, 1995 | [JP] | Japan | 7-058092 |
| Apr. 3, 1995 | [JP] | Japan | 7-102971 |

[51] Int. Cl.⁶ ......... G01N 37/00
[52] U.S. Cl. ......... 422/62; 422/63; 422/83; 422/103; 422/104; 285/137.1; 439/198
[58] Field of Search ......... 422/50, 62, 63, 422/83, 99, 103, 104; 436/43, 183; 285/137.1; 439/191, 194, 195, 198

[56] References Cited

U.S. PATENT DOCUMENTS

| 4,352,532 | 10/1982 | Hardin | 339/15 |
| 4,507,707 | 3/1985 | Willis | 361/380 |
| 4,840,574 | 6/1989 | Mills | 439/191 |
| 5,340,543 | 8/1994 | Annino et al. | 422/89 |
| 5,342,098 | 8/1994 | Wilkins | 285/26 |
| 5,405,269 | 4/1995 | Stupecky | 439/191 |

FOREIGN PATENT DOCUMENTS

3840941 A1  6/1989  Germany.

OTHER PUBLICATIONS

Auergesellschaft GmbH. "Fruherkennugn von Explosionsgefahren "LABO, 3. Jahrgang, Heft 1, Jan. 1972; p. 12.
Leybold–Heraeus; "Schnelle, Selektive und Kontinuierliche Analyse von Gasen unde Dampfen"; Nov. 1979.
J. Hengstenberg, B. Sturm, and O. Winkler. "Messen und Regeln in der Chemischen Technik"; Springer–Verlag 1964; 1458–1460.

*Primary Examiner*—Long V. Le
*Attorney, Agent, or Firm*—Oppenheimer Poms Smith

[57] ABSTRACT

A detachable gas analyzing apparatus has a plurality of gas analyzer units insertable into and removable from a the front side of a container case. Complementary electrical and gas connectors are disposed on the rear side of the gas analyzer units and the container case. Guides and engaging rails guide the gas analyzer units as they are inserted into the container case. The gas connectors are substantially self-aligning by the provision of complementary tapered portions formed on gas sockets and plugs. The gas connectors also align the electrical connectors and provide compensation for linear misalignment. A plurality of gas connectors may also be employed, forming a number of inward and outward gas passages.

13 Claims, 18 Drawing Sheets

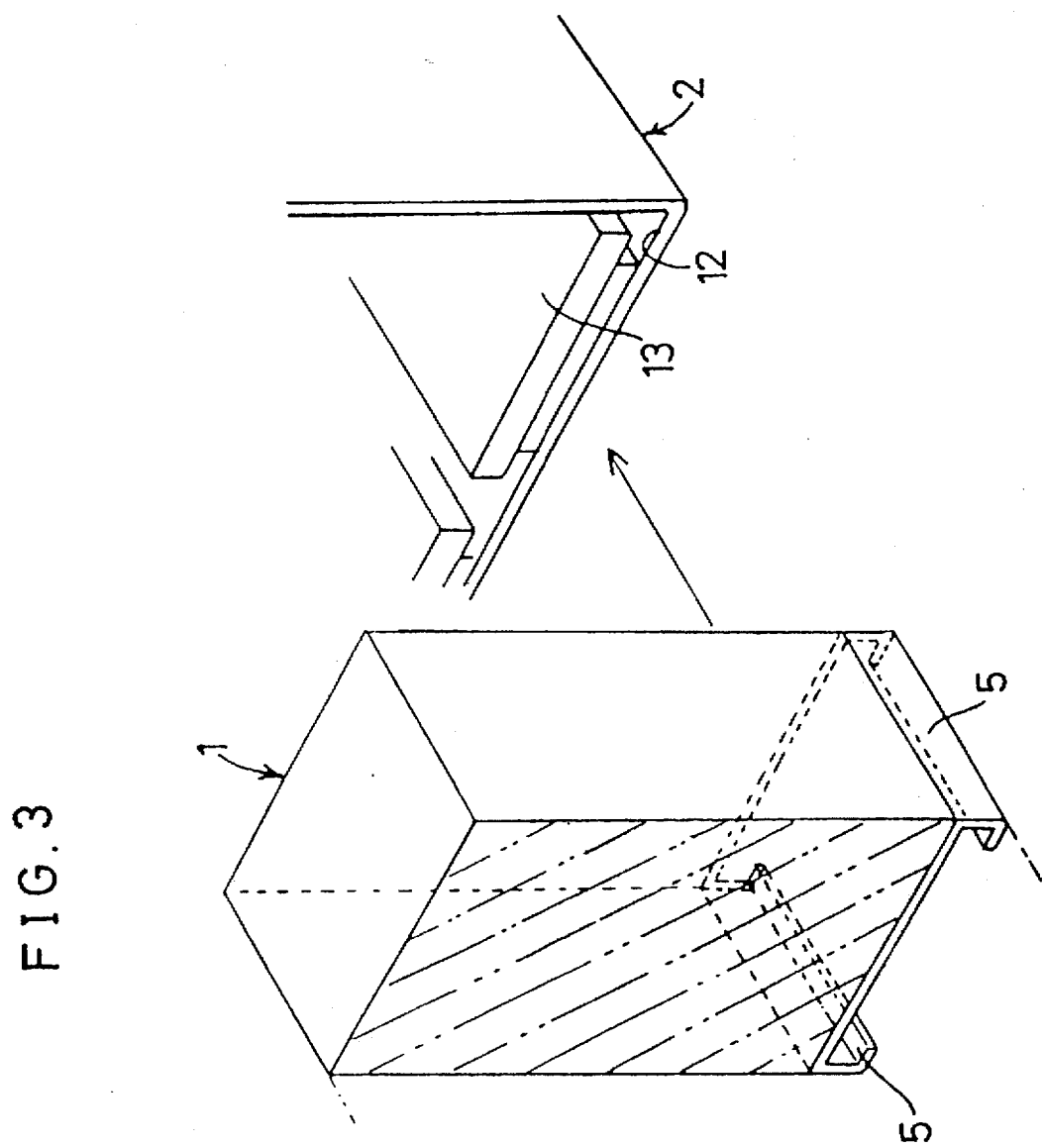

DETACHABLE GAS ANALYZING APPARATUS

BACKGROUND OF THE INVENTION

1. Field of the Invention

The present invention relates to gas analyzing apparatus and, more particularly, to gas analyzing apparatus in which a plurality of gas analyzer units are detachable from the front of the gas analyzing apparatus.

2. Description of Related Art

Conventional gas analyzing apparatus has plural electrical connectors for source power and for signal processing. A gas joint is provided on the back of the gas analyzer unit in a unitary structure with the gas analyzer. Each connector or joint is independently furnished with connecting and fixing mechanisms for electrical cable or gas piping, respectively.

In such conventional gas analyzing apparatus, when an individual gas analyzer unit is attached or detached, the operator needs to access the rear or back side of the gas analyzer unit to connect or separate, respectively, each connector and joint. This connecting and separating job is relatively complicated and requires the provision of working space behind the gas analyzer unit, thereby requiring a larger installation space for the gas analyzer unit.

SUMMARY OF THE INVENTION

In view of the drawbacks of conventional gas analyzing apparatus, it is a primary object of the present invention to provide a detachable gas analyzing apparatus capable of connecting and disconnecting electrical and gas connectors easily, securely, and safely from the front of the gas analyzer unit with inexpensive components while requiring only a small space for installation.

To achieve this object, the detachable gas analyzing apparatus of the present invention is characterized in the provision of electrical and gas connectors without independent or dedicated guiding, connecting, or fixing mechanisms. Complementary connectors are provided on the rear side of removable gas analyzer units and on the inner rear side of a container case in which the analyzer units are receivable.

One feature of the present invention is the provision of guides and complementary engaging rails respectively on the container case and the gas analyzer units. The guides and engaging rails guide the gas analyzer units as they are inserted and removed from the container case. The number of guides provided corresponds to the number of gas analyzer units to be received within the container case.

One aspect of the present invention is the provision of apparatus for releasably securing individual gas analyzer units in the container case. A screw is rotatably mounted in a front plate of the gas analyzer unit, and a nut member is threaded on the screw with a spring mounted between the front plate and the nut member, so that the nut member is movable responsively with the screw. A groove is formed in the container case with which the nut member is engageable. The gas analyzer unit may be secured in the container case by rotating the screw, thereby rotating the nut member to engage with the groove. Further rotation of the screw threads the screw into the nut member, securely drawing the gas analyzer unit into the container case.

One of the features of this securing apparatus is that the spring may be either a coil spring in a normally compressed state or a plate spring. The plate spring may have leg portions angularly extending from a planar portion, which leg portions contact the front plate of the gas analyzer unit, and which planar portion contacts the nut member.

Another aspect of the gas analyzing apparatus of the present invention is that a clamping member may be provided on the front of the container case. The clamping member is rotatable and has a roller which contacts an abutting member mounted to the front of the gas analyzer unit to urge the gas analyzer unit securely into the container case.

According to another aspect of the present invention, tapered portions may be formed on the gas connectors. The tapered portions are complementary with each other and self-align and guide the gas connectors and the electrical connectors when the gas analyzer unit is being inserted into the container case.

One of the safety features of the present invention is that the connection between the electrical connectors is not made until a seal is made in the gas connectors. Therefore, the chance of an electrical spark igniting leaking gas is greatly reduced. Further, a small gap or allowance is provided between the respective gas connectors after the electrical connectors have been completely engaged. The gap accommodates manufacturing and assembly errors and relative changes in the inserting and removing direction of the gas analyzer unit.

According to another aspect of the present invention, a coupler with a built-in gas stop mechanism may be provided. A gas stopping ball and a spring are provided in the gas connector of the container case with the spring urging the gas stopping ball against a seat in the connector to form a seal when the gas analyzer unit is not received in the container case. A pin is provided in the gas connector of the gas analyzer unit. When the gas analyzer unit is inserted into the container case, the pin urges the gas stopping ball away from the seat so that gas may pass therethrough.

A further aspect of the present invention is the provision of a coupler in which gas passages are formed. The coupler has a gas plug which may have a plurality of plug connectors with seal members disposed on the outer periphery thereof, and a gas socket which has a corresponding number of socket connectors. The plug and socket connectors are respectively formed within complementary plug and socket elements which sealingly enclose the plug and socket connectors. Gas passages are formed by respective pairs of gas and socket connectors and through an inner space defined by the plug and socket elements.

Yet another feature of the present invention is that the provision of the spring around the screw and between the nut member and the front plate allows an operator to secure the gas analyzer unit from the front of the apparatus as the nut member moves coincidently with the screw. Accordingly, the electrical and gas connections may be securely made without the need to access the back of the apparatus.

Another feature of the present invention is that the plate spring minimizes the size of the apparatus by reducing the distance between the front plate and the nut member.

Yet another feature of the present invention is that the gas connectors not only self-align and guide the electrical connectors, but also provide a small gap to compensate for changes in the relative position of the gas analyzer unit in the inserting and removing direction thereof.

One of the advantages of the gas analyzing apparatus of the present invention is that each of the gas analyzer units can be inserted and removed, as well as fixed and released, from the front side of the apparatus. Therefore, in contrast to prior art apparatus, an operator does not need to access the back of the gas analyzing apparatus in order perform these routine functions, saving on working and installation space of the apparatus. Furthermore, the electrical and gas connections may be made inexpensively without the need of expensive dedicated guiding mechanisms and safely without the need to access the rear of the apparatus. Moreover, as the guide is provided in the container case and the engaging rails are provided on the analyzer unit, the gas analyzer unit may be inserted and removed securely and smoothly, independent of and without interference from other gas analyzing units.

Additional advantages of the detachable gas analyzing apparatus of the present invention include space-saving design from both a construction and installation point of view, self-aligning and guiding gas connectors, and the elimination of dedicated guiding mechanisms and gas shut-off valve mechanisms. All of these features reduce the cost of manufacturing and assembling the detachable gas analyzing apparatus as well as improve the safety in operating the apparatus.

Additional aspects, features, and advantages of the present invention will become apparent to those skilled in the art from a reading of the following detailed description with reference to the accompanying drawings.

BRIEF DESCRIPTION OF THE DRAWINGS

FIG. 3 is a perspective view of the detachable gas analyzing apparatus;

DETAILED DESCRIPTION OF THE PREFERRED EMBODIMENTS

Figure 1:
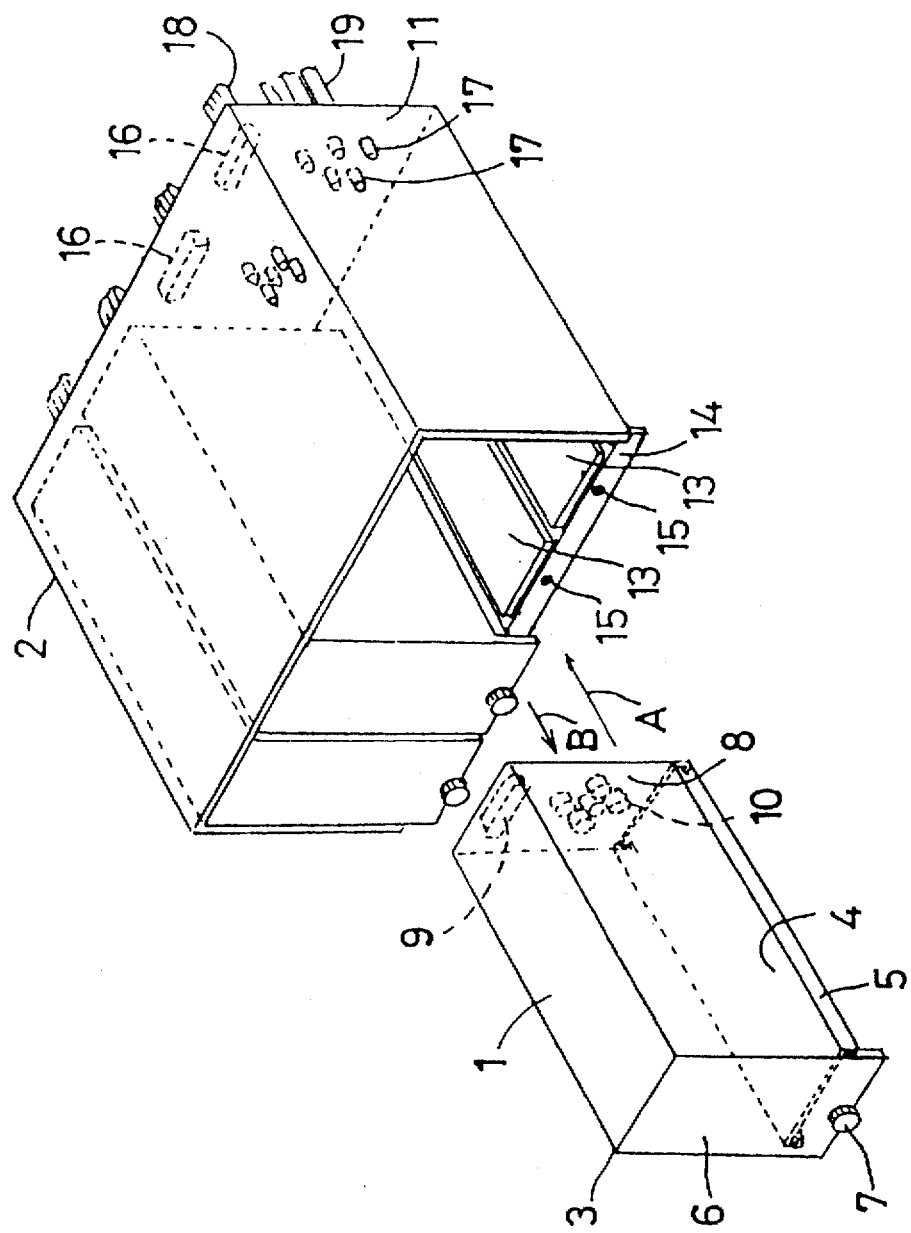
FIG. 1 is a perspective view showing an exemplary embodiment of a detachable gas analyzing apparatus of the present invention.
Figure 2:
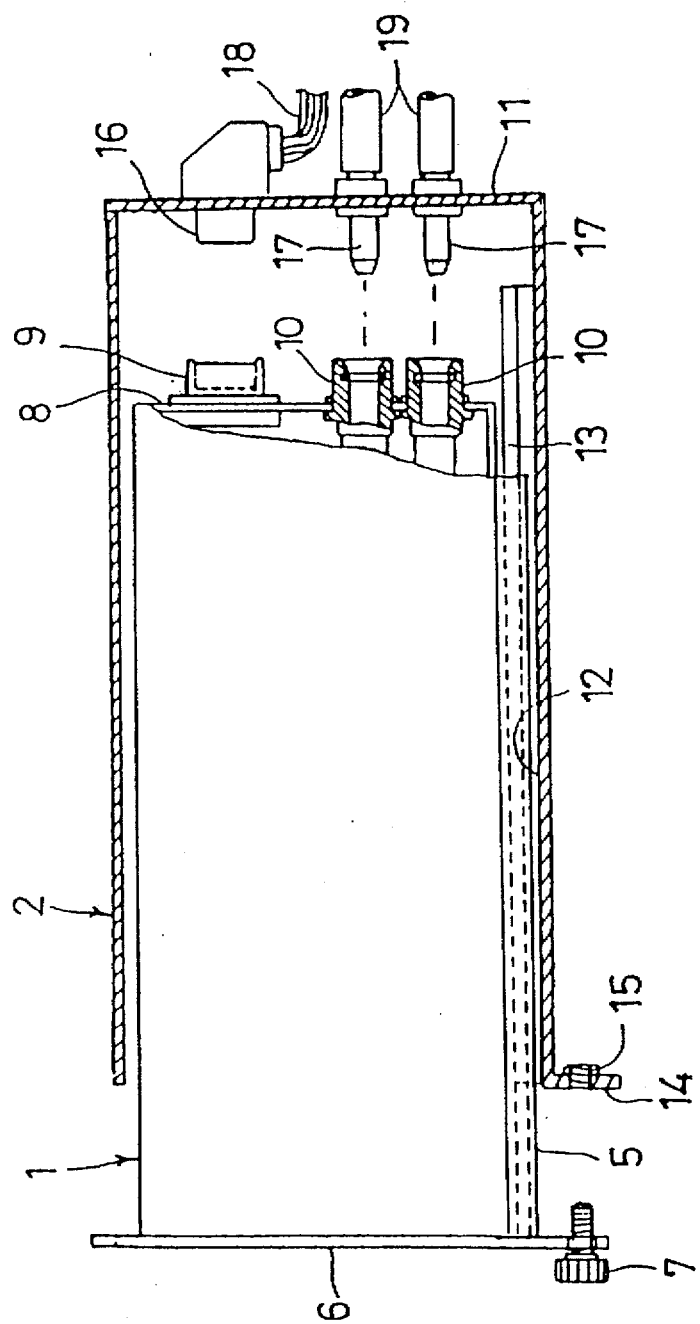
FIG. 2 is a sectional view of the detachable gas analyzing apparatus.

Referring to the drawings, An exemplary embodiment of a detachable gas analyzing apparatus of the present invention is illustrated in FIGS. 1 to 3. The detachable gas analyzing apparatus generally includes at least one but preferably a plurality of gas analyzer units 1 and a container case 2 for accommodating a plurality of the gas analyzer units 1 in, preferably, a mutually parallel state so that the gas analyzer units 1 can be inserted into or removed from the container case 2 independently.

Regarding exemplary structure of the gas analyzer units 1 in more detail, each gas analyzer unit 1 has a main body 3 which is made from suitable metal such as stainless steel, which main body 3 preferably has a rectangular, parallelepiped shape. The main body 3 is defined by a front, a rear, two sides, a top, and a bottom, with the main body 3 preferably only opening on one of these sides. The main body 3 incorporates a gas analyzing section including an infrared ray source, a gas cell, and a detector, preferably in this order, as well as a printed circuit board and other apparatus having signal-processing functions for processing signals from the detector.

The unit main body 3 has a lower plate along each side of which is formed an engaging portion in the form of an engaging rail 5. The engaging portions or rails 5 are slidably engageable with a guide 13 of the container case 2, guiding the gas analyzer unit 1 into the container case 2 as shown by the arrow. The main body 3 also has a front plate 6 in which is formed a hole for receiving a fixing screw 7, and a rear plate 8 on which are arranged an electrical connector 9 such as an electrical socket and a plurality of gas connectors 10 such as gas sockets, which gas sockets five are preferably shown. The electrical connector 9 is in communication with the printed circuit board of the signal-processing apparatus mentioned above, and the gas connector 10 is connectable to gas cell as discussed below.

Regarding the exemplary structure of the container case 2 in more detail, the container case 2 is preferably formed in a substantially rectangular box-like form with an opening in the front side thereof and a sufficient depth for accommodating the plurality of gas analyzer units 1, which units 1 four are shown in the exemplary embodiment, preferably in a mutually parallel state. The container case 2 is closed along the rear side thereof by a plate member 11, and is made from metal, preferably stainless steel.

The container case 2 has a bottom 12 on which the guides 13 are mounted. The guides 13, the number of which equal the number of analyzer units 1 to be received in the container housing 2, are disposed linearly and in parallel from the front side to the rear side of the container case 2 in a substantially spaced relationship. The front side of the bottom 12 is folded downward to form a folded portion 14 in which a threaded hole 15 is formed to releasably engage with the fixing screw 7 of one of the analyzer units 1.

The plate member 11 is provided in complementary and corresponding positions a corresponding plurality of electrical connectors 16 and gas connectors 17, each of which may respectively have electrical cable 18 and gas piping 19 connected rearwardly thereto. Each pair of electrical connector 16 and gas connector 17 of the container case 2 complement and engage with a corresponding pair of electrical connector 9 and gas connector 10 of the analyzer unit 1. Accordingly, as particularly shown in FIG. 2, either of the electrical connectors 9 and 16 and either of the gas connectors 10 and 17 may be male or female, such as a plug and socket as shown. Accordingly, the container case 2 is divided into a plurality of receiving bays each having a guide 13, an electrical connector 16, and a gas connector 17 for removably receiving a gas analyzer unit 1 having complementary guide rails 5, an electrical connector 9, and a gas connector 10.

All of the electrical and gas connectors 9, 10, 16, and 17 are preferably releasable, as mentioned above, without any fixing mechanism. A commercially available example of such electrical connectors is a D-Sub connector produced by Fujitsu, and a commercially available example of such gas connectors is a multicoupler produced by Nitto Koki.

Figure 4A:
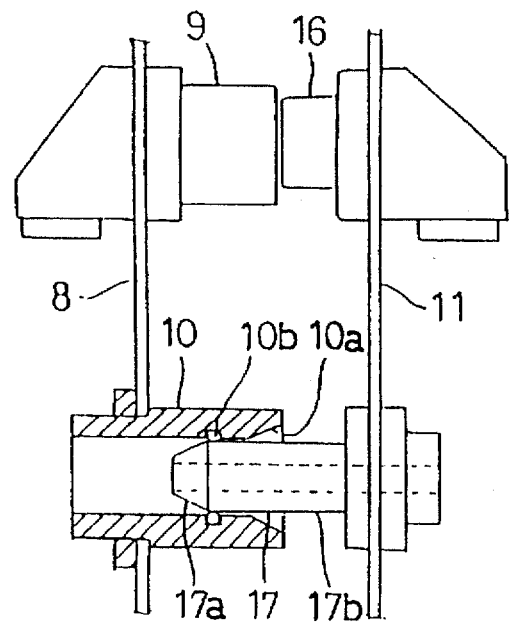
FIGS. 4A and 4B are partial cross-sectional views illustrating the relationship between an electrical connector and a gas connector in exemplary embodiments of the detachable gas analyzing apparatus.
Figure 4B:
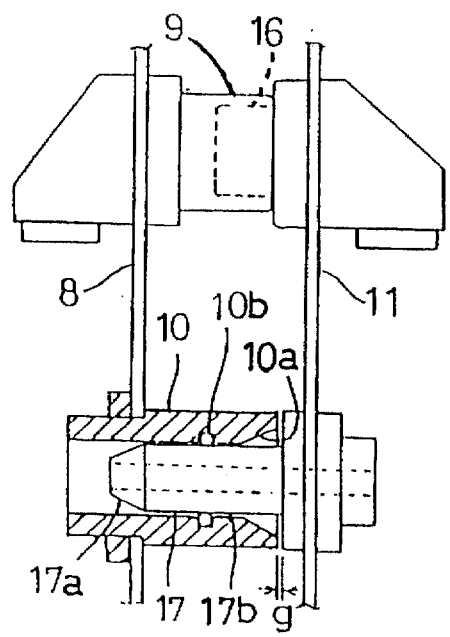
Figure 5:
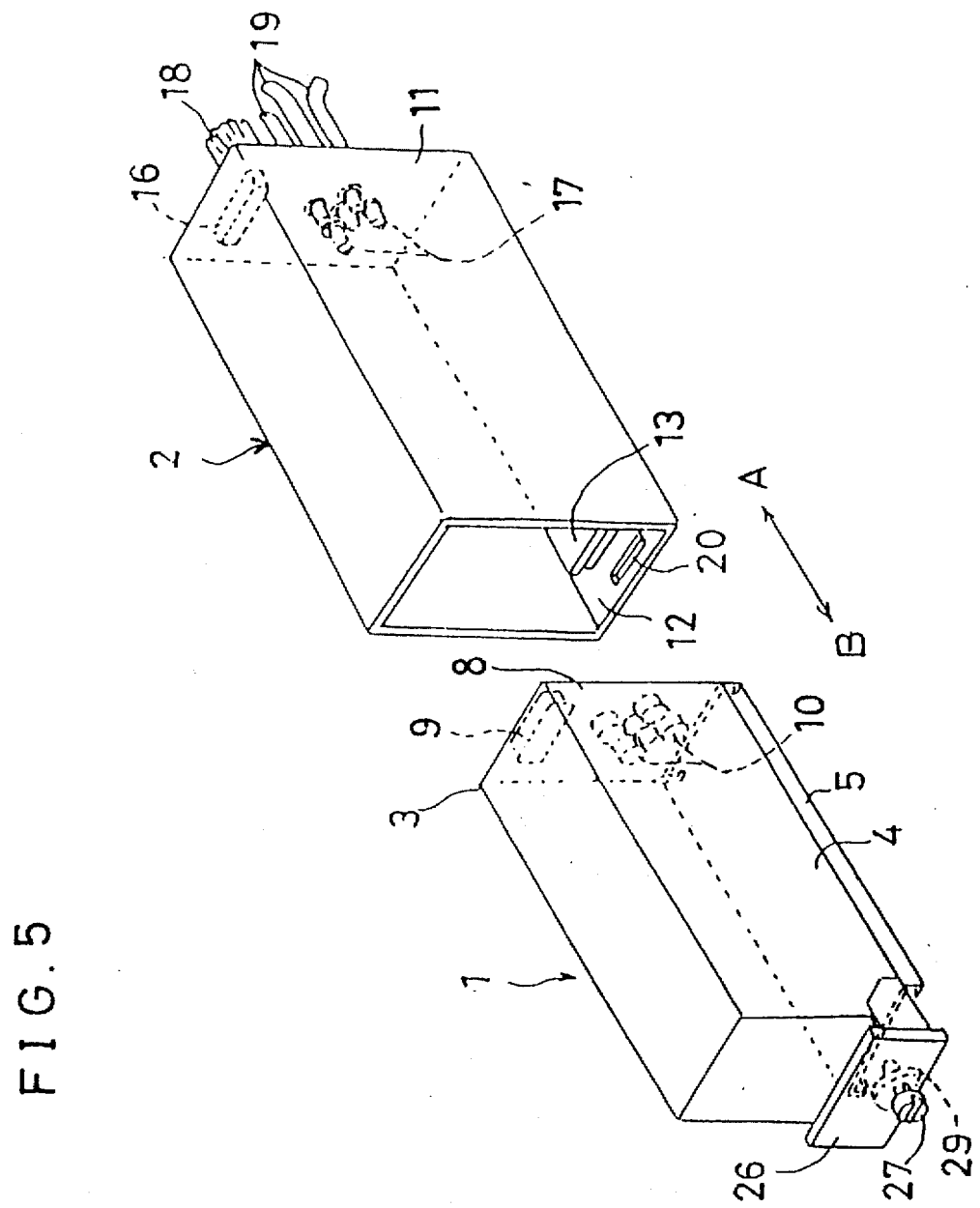
FIG. 5 is a perspective view showing another exemplary embodiment of a detachable gas analyzing apparatus of the present invention.
Figure 6:
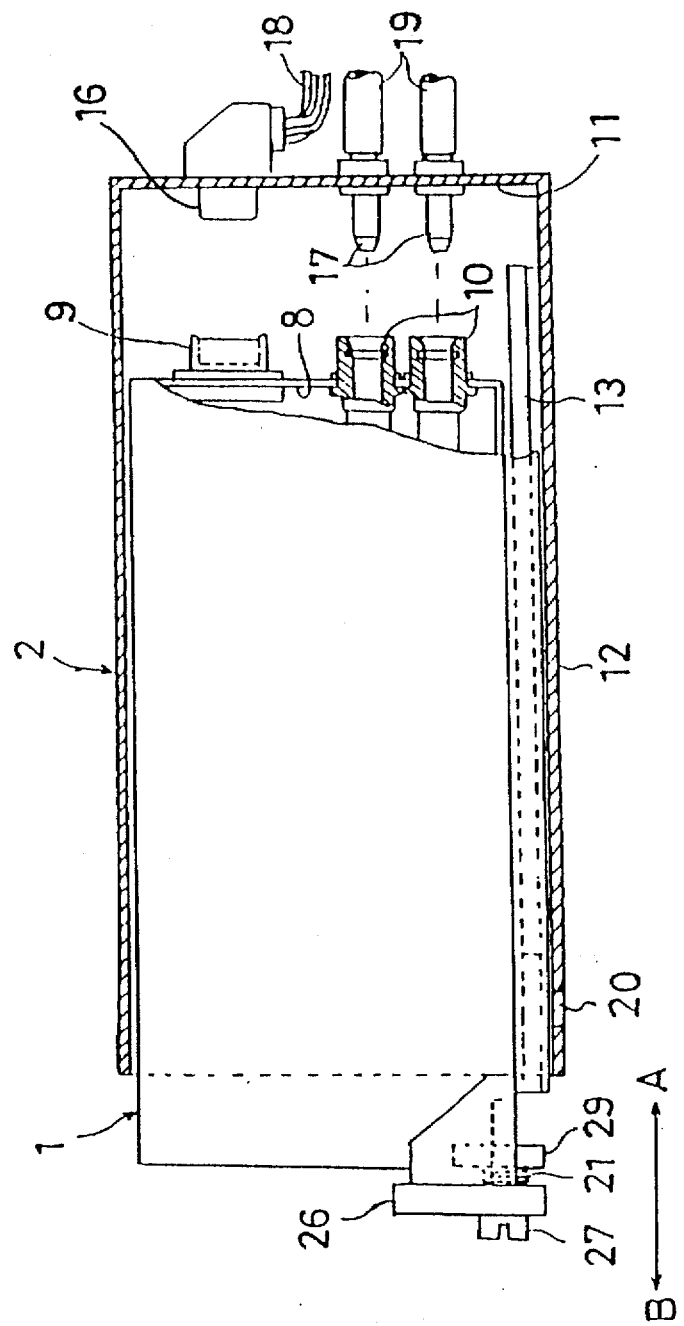
FIG. 6 is a sectional view of the detachable gas analyzing apparatus shown in FIG. 5.

With reference to FIGS. 4A and 4B, the gas socket 10 (shown in cross section) and the gas plug 17 are shown in more detail. The socket 10 has a tapered portion 10a corresponding and providing guidance to and a tapered portion 17a of the plug 17. The gas socket 10 has an inner surface in which is formed a groove for receiving a seal member 10b such as an O-ring. The gas plug 17 has an outer periphery defining a drum portion 17b which is sealingly receivable through the seal member 10b to provide a tight seal for the gas connector. Shown in phantom line, the gas plug 17 has an inner bore for the passage of gas therethrough.

Regarding the connection of the electrical socket 9 and the electrical plug 16, after the tapered portion 17a of the gas plug 17 passes through the seal member 10b of the gas socket 10, with the drum portion 17b forming a tight seal with the seal member 10b, the electrical plug 16 engages with the electrical socket 9. When the plug 16 (shown in phantom line in FIG. 4B) is completely engaged with the socket 9, there remains a small gap or tolerance g between the end or rear face of gas socket 10 and the base of the gas plug 17.

With continued reference to FIGS. 1 to 4, to place a gas analyzer unit 1 in the container case 2, a user firstly ensures that a stop valve (not shown in the drawings) positioned in stream with the gas piping 19 is closed. The gas analyzer unit 1 is then inserted into one of the receiving bays of the container case 2 with the engaging rails 5 slidably engaging the guide 13 on the bottom 12 of the container case 2. A proper force is applied on the front plate 6 in the direction indicated by arrow A in FIG. 1 to linearly slide the unit 1 on the guide 13.

In order to securely engage the electrical and gas connectors 9 and 10 with the complementary connectors 16 and 17, it is necessary to properly position the connectors 9 and 10 relative to connectors 16 and 17. In related conventional apparatus, a guide mechanism including a guide pin and a guide hole are provided to connect firmly and smoothly commonly used connectors. However, in order to achieve an accurate connection, high precision and strict tolerance is required in machining and assembling the gas analyzer unit 1 and the various engaging components.

If a highly precise, dedicated guide mechanism is not provided, there is a possibility that the relative position in the insert and remove directions (i.e., arrows A and B in FIG. 1) of the connectors 9, 10, 16, and 17 will change over time and use, resulting in faulty connections, due to errors in machining and assembling the components. For example, although a sufficient connection is made between the gas connectors 10 and 17, there may be a faulty connection between the electrical connectors 9 and 16, or vice versa. Accordingly, by providing the relatively inexpensive configuration of the electrical connectors 9 and 16 (and the gas connectors 10 and 17) as described above, the electrical connection is performed firmly and safely in the absence of dedicated guiding mechanisms.

Expanding upon these connections further with particular reference to FIGS. 4A and 4B, with the provision of the complementary tapered portions 10a and 17a on the respectively connecting ends of the gas socket and plug 10 and 17, there is a certain amount of play which the tapered portions 10a and 17a correct by guiding and urging the gas plug 17 into the gas socket 10 even though the plug 17 is not precisely in line with the socket 10. In other words, the gas plug and socket 10 and 17 are self-aligning. In addition, just after the tapered portion 17a has passed through the seal member 10b, as shown in FIG. 4A, thereby sealing the drum portion 17b in the seal member 10b, the connection between the electrical socket and plug 9 and 16 begins to be made. Accordingly, not only to the gas connectors 10 and 17 serve as a guide for and self-align themselves, but the gas connectors 10 and 17 also serve as guides for the electrical connectors 9 and 16, thereby eliminating the need for dedicated guiding components or mechanisms.

Further, the connectors 9, 10, 16, and 17 are configured so that when the electrical plug 16 is completely received within the electrical socket 9, there is still the small gap g between the gas connectors 10 and 17. Therefore, if there is a change in the relative position in the inserting direction, the gap g allows for this change to ensure that a proper electrical connection is made, absorbing or accommodating for the change in relative position.

With the gas and electrical connectors in a connected state, the fixing screw 7 is driven into the threaded hole 15 to secure the gas analyzing unit 1 in the container case 2 and to ensure that the electrical and gas connections remain secure.

To remove the gas analyzing unit 1 from the container case 2 for analysis, the stop valve (not shown) on the gas pipes 19 is closed; the fixing screw 7 is loosened; and the gas analyzer unit 1 is drawn out of the receiving bay of the container case 2 in the direction of arrow B in FIG. 1. As a result, the electrical connectors 9 and 16 and the gas connectors 10 and 17 are disconnected as the gas analyzer unit 1 slides linearly along the guide 13.

By providing the gas analyzing apparatus of the present invention with such a configuration, each of the gas analyzer units 1 can be inserted and removed, as well as fixed and released, from the front side of the apparatus. Therefore, in contrast to prior art apparatus, an operator does not need to have access to the back of the gas analyzing apparatus in order perform these routine functions, saving on working and installation space of the apparatus. Furthermore, the electrical and gas connections may be made inexpensively without the need of expensive dedicated guiding mechanisms and safely without the need to access the rear of the apparatus. Moreover, as the guide 13 is provided in the container case 2 and the engaging rails 5 are provided on the analyzer unit 1, the gas analyzer unit 1 may be inserted and removed securely and smoothly, independent of and without interference from other gas analyzing units.

The present invention is not to be limited to the embodiments specifically described herein. For example, the unit main body 3 of the analyzing unit 1 may be any desired shape as long as the gas analyzer and the printed circuit board can be mounted, and the gas analyzer unit may be inserted and remove without deformation. Further, the configuration of the guide 13 and the engaging rails 5 may take any form which allows the gas analyzer unit 1 to be inserted and removed linearly. For example, a groove may be formed on the inner side of the container case 2 and a complementary engaging portion such as a protrusion may be formed on the outer side of the gas analyzer unit 1 to slidingly engage with the groove.

With reference to FIGS. 5 through 8, an exemplary embodiment of the gas analyzing apparatus is shown in accordance with the present invention, particularly a mechanism for securing the gas analyzer unit 1 to the container case 2. Reference numerals in FIGS. 5 through 8 the same as those in FIGS. 1 through 4 indicate like parts so that description thereof will be omitted herein.

In this exemplary embodiment, the gas analyzer unit 1 has a front plate 26 provided with a screw 27. The screw 27 passes through the front plate 26 and rotates about an axis parallel to insert/remove directions of the unit 1 shown by arrows A and B. The screw 27 is rotatably mounted in that the screw 27 may rotate idly or freely without advancing through the front plate 26. An E-ring 28 may be provided in the front plate 26 through which the screw 27, which is preferably in the form of a threaded bolt, passes. The E-ring 28 prevents the screw 27 from inadvertently dislodging from the front plate 26.

Figure 8:
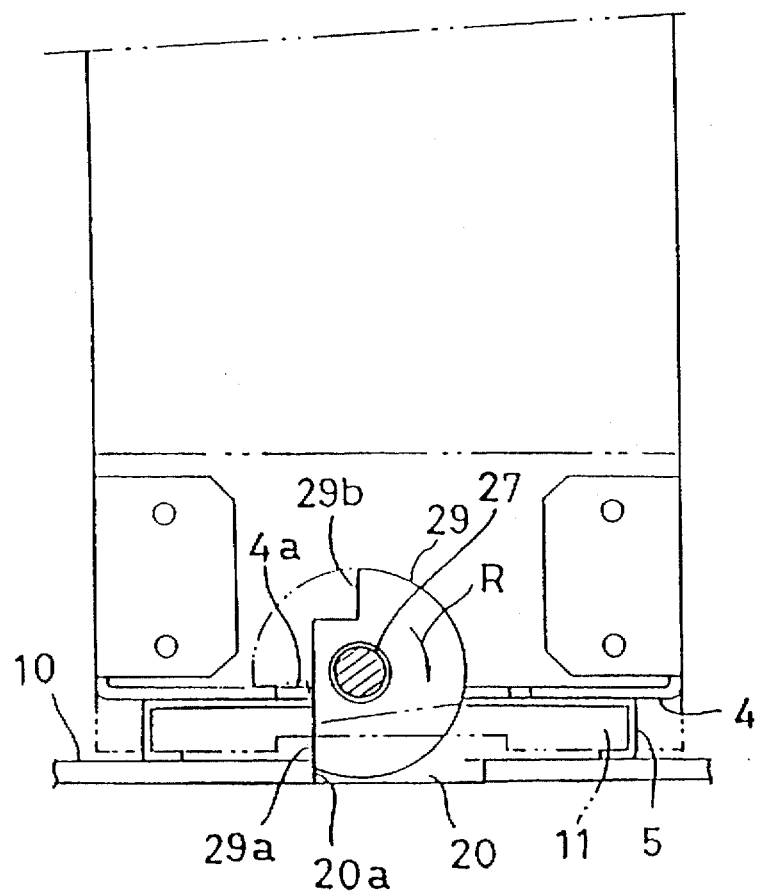
FIG. 8 is a sectional front view illustrating the principal parts of the detachable gas analyzing apparatus.
Figure 9:
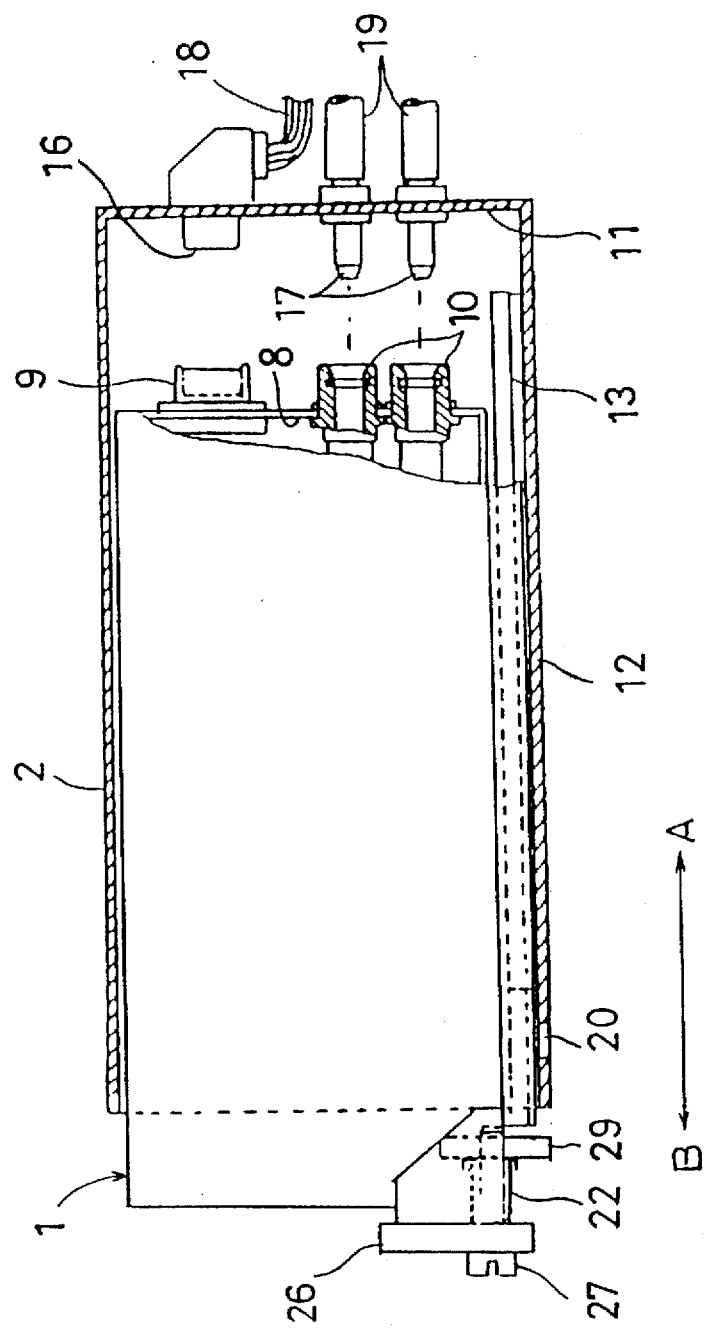
FIG. 9 is a sectional view showing a further exemplary embodiment of a detachable gas analyzing apparatus in accordance with the present invention.

With particular reference to FIG. 8, the screw 27 is threadingly engaged with a disc-shaped nut member 29 which is preferably cut into a key shape. The nut member 29 has a first abutting part 29a which abuts a peripheral wall 20a of a groove 20 formed in the front side of the guide 13 on the bottom 12 of the container case 2 when the nut member 29 is rotated in a direction indicated by arrow R. The nut member 29 also has a second abutting part 29b which abuts an upper surface 4a of the bottom plate 4 of the gas analyzer unit 1 when the nut member 29 is rotated in a direction opposite to that indicated by arrow R.

Figure 7:
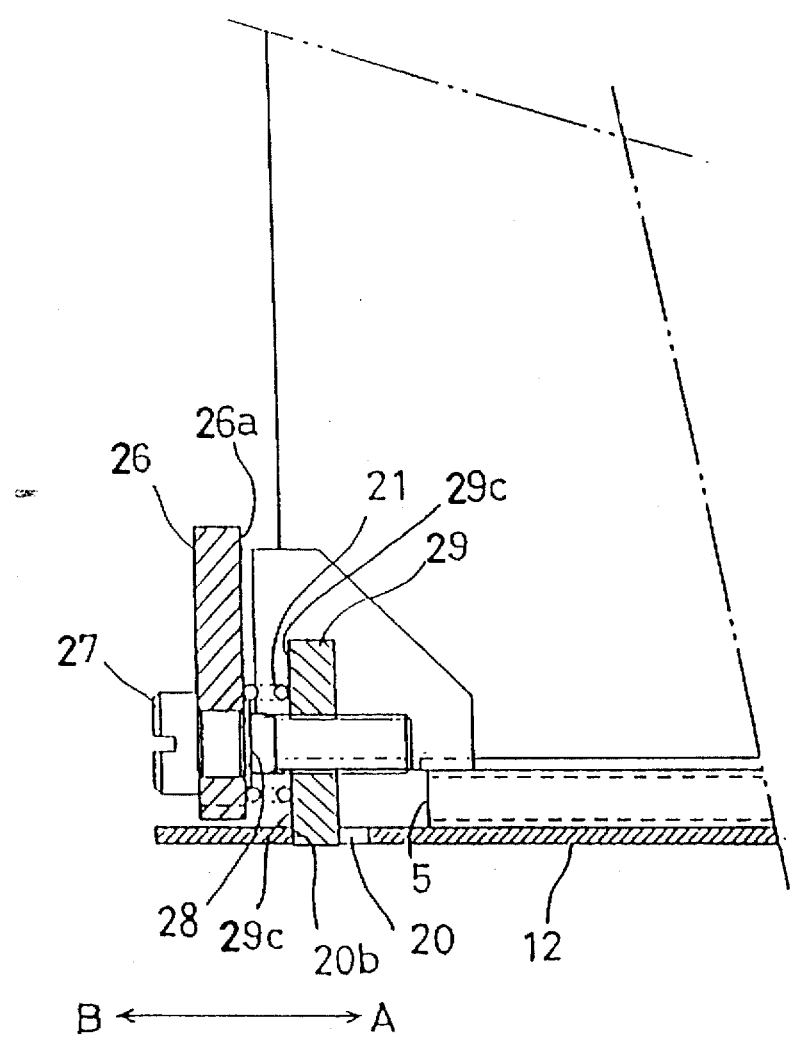
FIG. 7 is an enlarged sectional view illustrating principal parts of the detachable gas analyzing apparatus.

With particular reference to FIG. 7, a spring member such as a coil spring 21 is disposed around the screw 27 and positioned between a near side 26a of the front plate 26 and a planar surface 29c of the nut member 29. The coil spring 21 urges the nut member 26 to move responsively to the movement of the screw 27; that is, the nut member 29 rotates when the screw 27 rotates.

In operation, if the gas connectors 10 and 17 are not provided with dedicated gas stopping mechanisms, an external stop valve (not shown) provided on the gas piping 19 is firstly closed before the gas analyzer unit 1 is inserted into the container case 2. As the gas analyzer unit 1 is inserted, the engaging rails 5 engage with the guide 13, as described above. During this process, the first abutting part 29a of the nut member 29 should be in a substantially horizontal position (see FIG. 1). When the analyzer unit 1 is completely inserted into the container case 2 with the electrical connectors 9 and 16 and the gas connectors 10 and 17 completed engaged and connected, the nut member 29 is located at a point substantially above the groove 20.

At this position, by rotating the screw 27 in the direction of arrow R (see FIG. 8), the nut member 29 rotates likewise and enters the groove 20 with the first abutting part 29a of the nut member 29 eventually abutting the peripheral wall 20a, thereby stopping the rotation of the nut member 29.

With particular reference to FIG. 7, as the screw 27 and the nut member 29 are threadingly engaged, further rotation of the screw 27 in the direction of arrow R draws the nut member 29 in the direction of arrow B until the planar surface 29c of the nut member 29 abuts a peripheral wall 20b of the groove 20. At this point, the nut member 29 is prevented from further linear or axial movement. Accordingly, still further rotation of the screw 27 in the direction of arrow R will urge the gas analyzer unit 1 in the direction of arrow A, thereby urging the gas analyzer unit 1 against the rear side of the container case 2. By urging the analyzer unit 1 in this manner, the electrical and gas connectors 9 and 10 of the unit 1 are securely urged into the corresponding electrical and gas connectors 16 and 17 of the container case 2. Accordingly, the gas analyzer unit 1 is detachably but securely fixed and accommodated in the container case 2 with firm and proper electrical and gas connections.

To remove the gas analyzer unit 1, any external gas stopping valves are firstly closed, and then the screw 27 is rotated in a direction opposite to that indicated by arrow R. Associated with this rotation, the nut member 29 will be urged slightly in the direction of arrow A until the force applied by the coil spring 21 is greater than the frictional forces between the planar surface 29c of the nut member 29 and the peripheral wall 20b of the groove 20, at which time the nut member 29 rotates in the same direction of the screw 27, i.e., opposite to arrow R, until the second abutting part 29b abuts the upper surface 4a of the bottom plate 4, thereby preventing further rotation of the nut member 29. The gas analyzer unit 1 may now be drawn out of the container case 2 in the direction of arrow B, disconnecting the electrical and gas connections in the process.

As was the case in the previously described exemplary embodiment, the gas analyzer unit 1 can be advantageously inserted and removed from the container case 2 by only having access to the front of the apparatus. Therefore, there is no need to access the back of the apparatus, thereby saving on working and installation space and eliminating useless dead space. Further, by configuring the nut member 29 to move linearly in the insert/remove direction of the gas analyzer unit 1, the gas and electrical connections are improved. Still further, by providing the coil spring 21 between the rear side 26a of the front plate 26 and the planar surface 29c of the nut member 29, the nut member 29 moves coincident with the screw 27, with the first and second abutting parts 29a and 29b minimizing wasteful movement of the nut member 29.

With reference to FIGS. 9 through 12, a further exemplary embodiment of the present invention is illustrated in which an alternative to the coil spring 21 disposed between the front plate 26 and the nut member 29 is provided. More specifically, a plate spring 22 is provided between the front plate 26 and the nut member 29, allowing correlative movement of the nut member 29 responsive to the movement of the screw 27.

Figure 10:
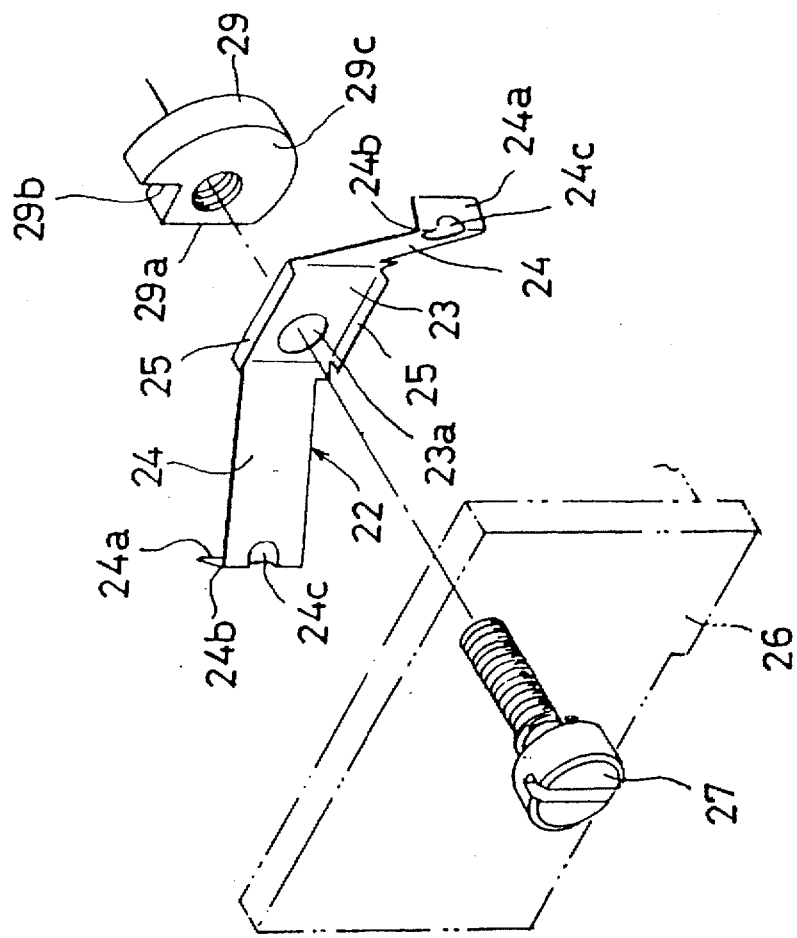
FIG. 10 is an exploded view illustrating exemplary fastening means according to the present invention.

With particular reference to FIG. 10, the plate spring 22 includes a planar portion 23 which abuts the planar surface 29c of the nut member 29 and leg portions 24 extending in a moderately inclined direction from both sides of the planar portion 23. Each leg portion 24 has a substantially perpendicular end portion 24a defining a crease 24b and a slot 24c centered about the crease 24b. Alternatively, the end portions 24a may be bent to be substantially coplanar with the front plate 26. Bent portions 25 are formed on sides of the planar portion 23 other than the sides from which the leg portions 24 extend and are substantially perpendicular to the planar portion 23. A hole 23a is formed slightly off center in the planar portion 23 through which the screw 27 passes.

Figure 11A:
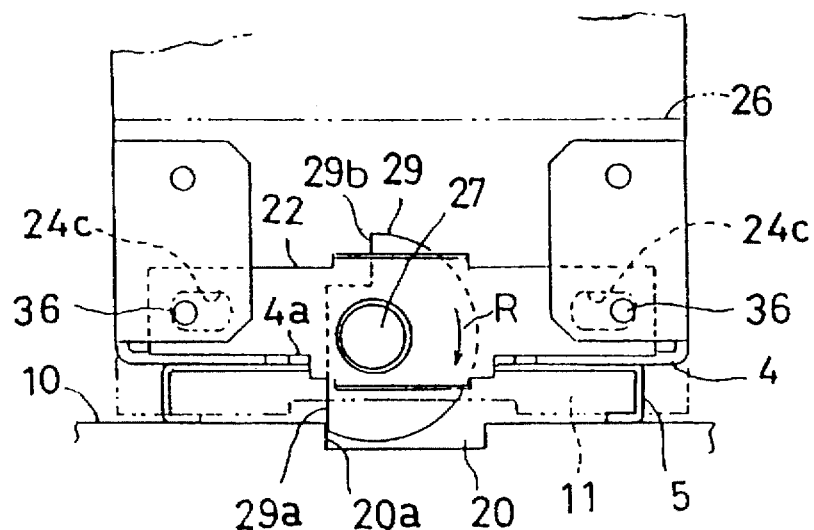
FIG. 11A is a front sectional view and FIG. 11B is a side sectional view illustrating principal parts of the detachable gas analyzing apparatus.
Figure 11B:
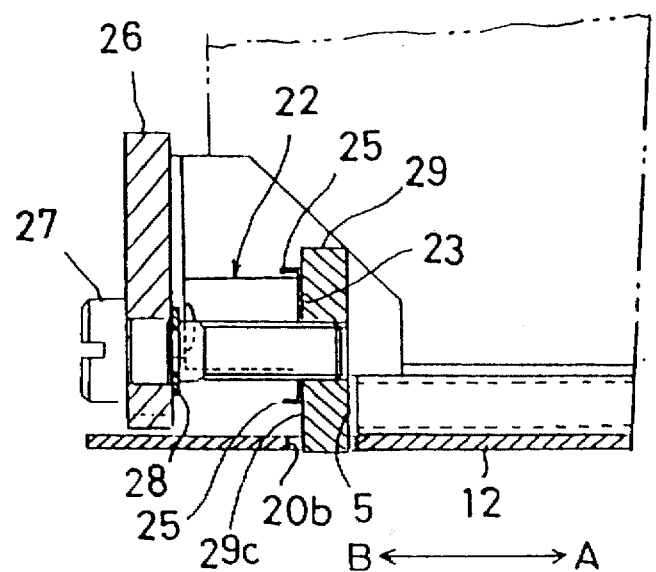
Figure 12A:
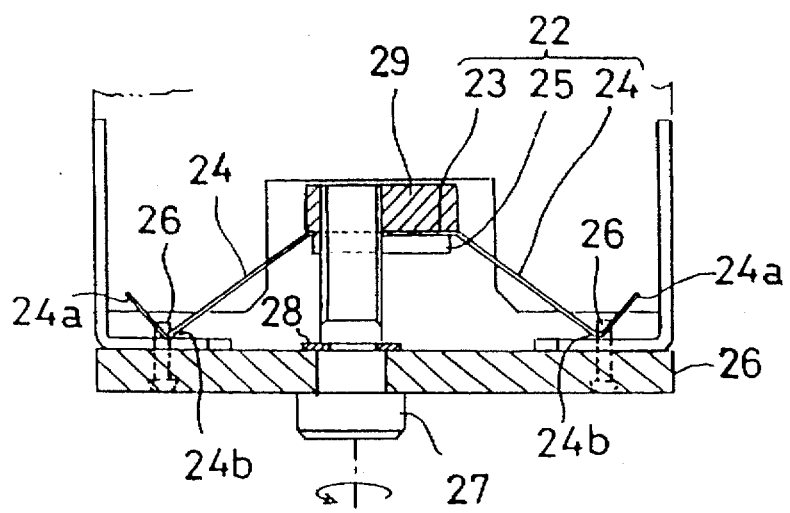
FIGS. 12A and 12B are sectional views illustrating the operation of the present invention, respectively showing uncompressed and compressed states of a plate spring.
Figure 12B:
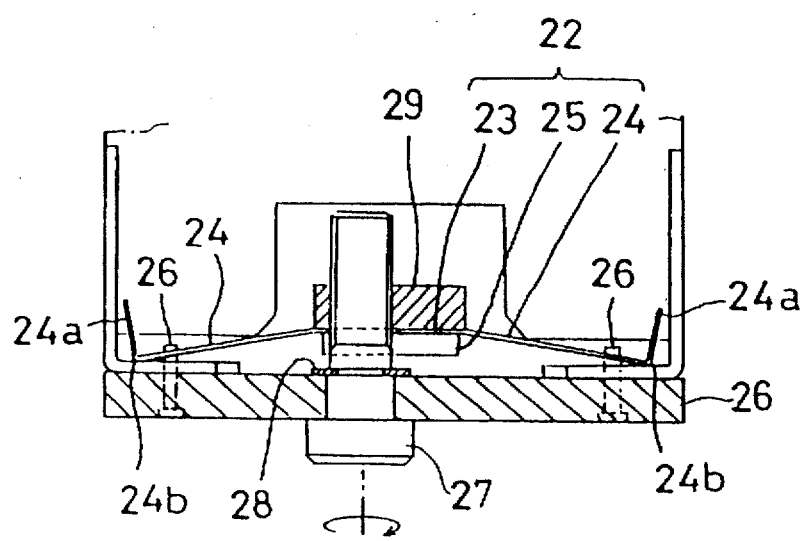

With particular reference to FIGS. 11 and 12, the plate spring 22 is provided between the front plate 26 and the nut member 29 with the screw 27 passing through the hole 23a. An outer surface of the planar portion 23 abuts the planar surface 29c of the nut member 29. Fixing pins 36 provided on the inner side of the front plate 26 are respectively slidably received in the slots 24c of the leg portions 24.

In operation, to insert the gas analyzer unit 1 according to this exemplary embodiment, the operator firstly closes any external gas valves on the gas piping 19 and then engages the engaging portions or rails 5 with the guide 13. As the analyzer unit 1 is inserted into the container unit 2, the first abutting part 29a of the nut member 29 should be substantially horizontal. When the analyzer unit 1 is completely inserted into the container case 2 with the electrical connectors 9 and 16 and the gas connectors 10 and 17 completed engaged and connected, the nut member 29 is located at a point substantially above the groove 20.

With particular reference to FIGS. 11A and 11B, by rotating the screw 27 in the direction of arrow R, the nut member 29 is urged in the direction of arrow B as the screw 27 and the nut member 29 are in threaded engagement. When the nut member 29 has linearly moved a sufficient distance, the first abutting part 29a thereof enters the groove 20. Further rotation of the screw 27 rotates the nut member 29 until the first abutting part 29a contacts the peripheral wall 20a of the groove 20, as shown in FIG. 11A. Continued rotation of the screw 27 in the direction of arrow R will now draw the nut member 29 in the direction of arrow B until the planar surface 29a of the nut member 29 contacts the peripheral wall 20b of the groove 20.

At this point, further rotation of the screw 27 will urge the front plate 26 and the gas analyzer unit 1 in the direction of arrow A, thereby urging the gas analyzer unit 1 against the rear side of the container case 2. Accordingly, the gas analyzer unit 1 is fixed in the container case 2 in a state in which the gas analyzer connectors 9 and 10 are tightly connected to the container case connectors 16 and 17, respectively.

To remove the gas analyzer unit 1 from the container case 2, any external gas stopping valves are firstly closed, and then the screw 27 is rotated in a direction opposite to that indicated by arrow R. Associated with this rotation, the nut member 29 will be urged slightly in the direction of arrow A until the force applied by the plate spring 22 is greater than the frictional forces between the planar surface 29c of the nut member 29 and the peripheral wall 20b of the groove 20, at which time the nut member 29 rotates in the same direction of the screw 27, i.e., opposite to arrow R, until the second abutting part 29b abuts the upper surface 4a of the bottom plate 4, thereby preventing further rotation of the nut member 29. The gas analyzer unit 1 may now be drawn out of the container case 2 along the guide 13 in the direction of arrow B, disconnecting the electrical and gas connections in the process.

Regarding the plate spring 22 in more detail, the planar portion 23 of the plate spring 22 abuts the nut member 29 with the bent portions 25 substantially perpendicular thereto. Accordingly, the area of the plate spring 23 abutting the nut member 29 is secured regardless of the bending state of the plate spring 22. Thus, the nut member 29 is able to firmly follow the movement of the screw 27. The provision of the bent portions 25 also prevents the legs portions 24 from bending beyond the elastic break limit thereof. In addition, the slots 24c of the leg portions 24 respectively receive the pins 36, thereby effectively preventing the plate spring 22 from rotating when the screw 27 is rotating.

As was the case in the previously described exemplary embodiments, the gas analyzer unit 1 can be advantageously inserted and removed from the container case 2 by only having access to the front of the apparatus. Therefore, there is no need to access the back of the apparatus, thereby saving on working and installation space and eliminating useless dead space. Further, by configuring the nut member 29 to move linearly in the insert/remove direction of the gas analyzer unit 1, the gas and electrical connections are improved. Still further, by providing the plate spring 22 between the rear side 26a of the front plate 26 and the planar surface 29c of the nut member 29, the nut member 29 moves coincident with the screw 27, with the first and second abutting parts 29a and 29b minimizing wasteful movement of the nut member 29. Also, the distance between the front plate 26 and the nut member 29 may be relatively small, thereby minimizing the overall size of the apparatus.

Figure 13:
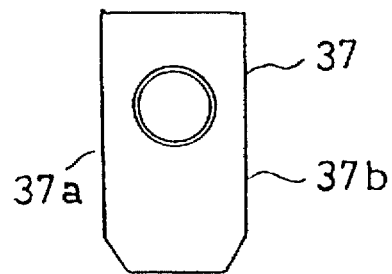
FIG. 13 is a view showing an exemplary embodiment of a nut member according to the present invention.

Referring to FIG. 13, an alternative exemplary embodiment to the nut member 29 is illustrated. In this embodiment, an oblong-shaped nut member 37 is disposed about the screw 27 and has a first abutting part 37a and a second abutting part 37b which function analogously to those respectively elements of the nut member 29 described above.

Figure 14:
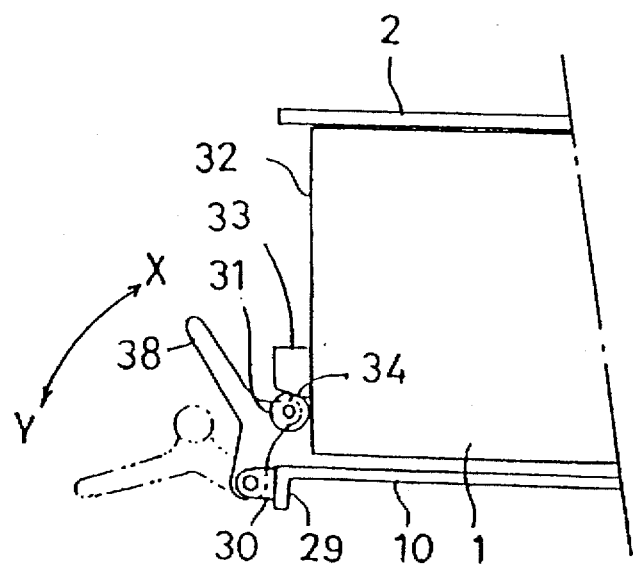
FIG. 14 is a side view showing principal parts of a detachable gas analyzing apparatus in accordance with the present invention.

A further exemplary embodiment of the gas analyzing apparatus of the present invention is illustrated in FIG. 14. In this embodiment, the container case 2 is provided a clamping element 28 which is preferably in the shape of a boomerang. The clamping element 38 is pivotally supported by a bracket 30 provided on a bent portion 29 of the front side of the container case 2. The clamping element 38 has a roller 31 disposed on the vertex-like portion thereof. The gas analyzer unit 1 is provided with an abutting element 33 at a position on the lower side of a front panel 32. The abutting element 33 has a tapered surface 34 formed on a lower side thereof, which tapered surface 34 inclines upwardly and outwardly from the front panel 32 and on which the roller 31 contacts.

As shown in FIG. 14, to firmly secure the gas analyzer unit 1 within the container case 2 with the respective electrical and gas connectors 9, 10, 16, and 17 securely coupled together, the clamping element 38 is rotated from the position shown in phantom line toward the front panel 32 in the direction indicated by arrow X, with the roller 34 contacting and pushing against the inclined surface of the abutting element 33, thereby urging the gas analyzer unit 1 into the container case 2. To remove the analyzer unit 1, the clamping element 38 is rotated away from the front panel 32 in the direction of arrow Y. Accordingly, the gas analyzer unit 1 may be easily fixed in or released from the container unit 2 without the use of tools from the front of the apparatus.

Figure 15A:
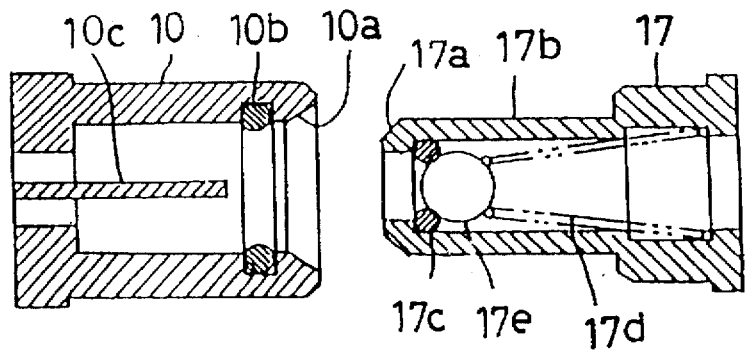
FIGS. 15A, 15B, and 15C are cross-sectional views showing an exemplary embodiment of a gas connector and the operation thereof in accordance with the present invention.
Figure 15B:
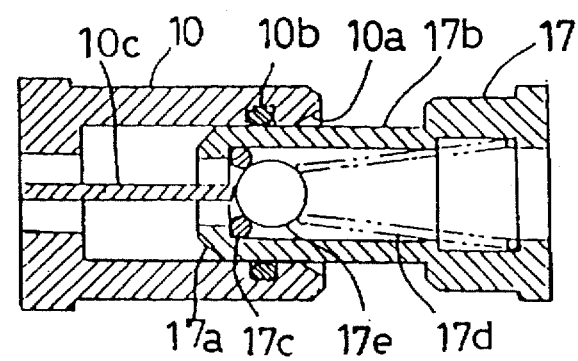
Figure 15C:
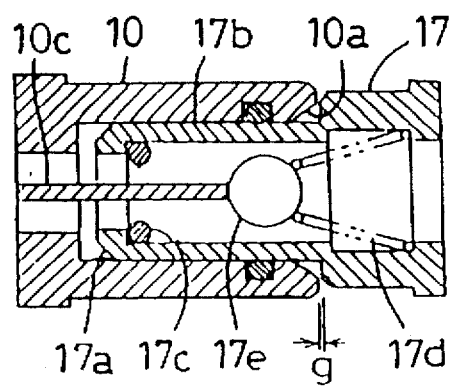
Figure 16:
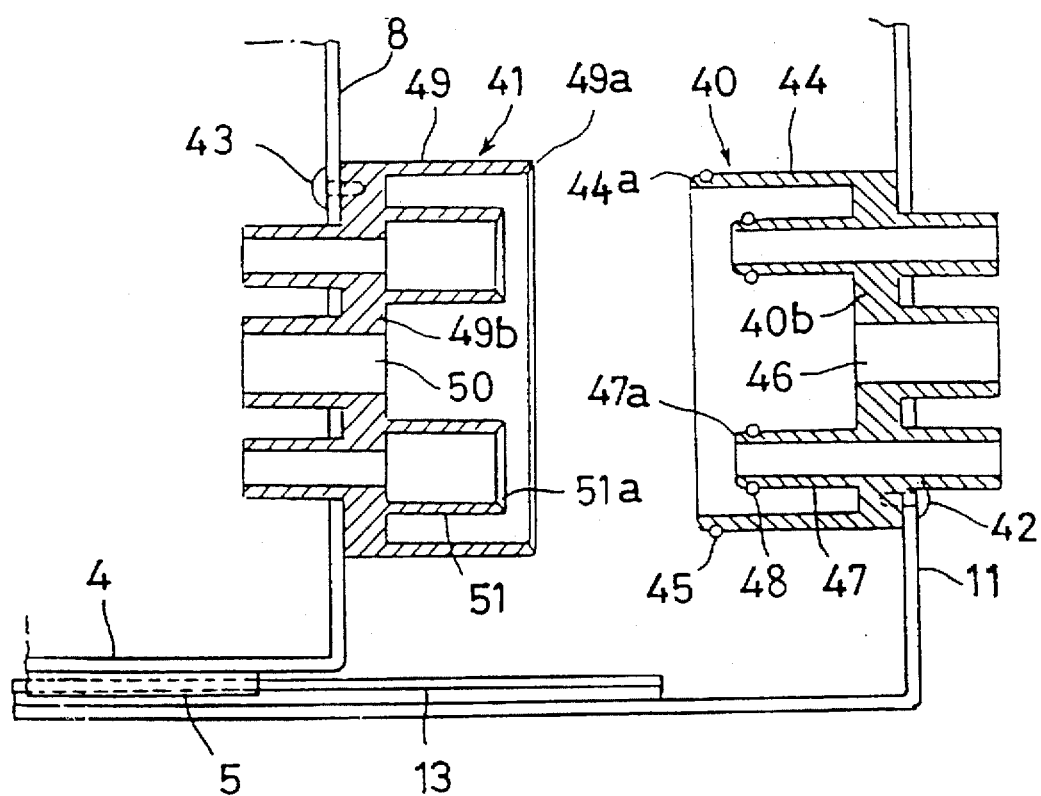
FIG. 16 is a sectional view showing another exemplary embodiment of a gas connector of the present invention.

Heretofore, the description of the present invention has focussed on exemplary embodiments of gas analyzing apparatus which were not provided with a dedicated gas stopping mechanism. However, the present invention also provides gas analyzing apparatus with a gas stopping device as illustrated in FIGS. 15A to 15C. As described with relation to FIGS. 1 to 4, reference numeral 10 refers to a gas socket with a tapered portion 10a on the connection end thereof and a seal member 10b disposed in an inner groove near the tapered portion 10a, and reference numeral 17 refers to a gas plug 17 with a tapered portion 17a on the connection end thereof and a drum portion 17b which slidably and sealingly engages with the seal member 10b of the gas socket 10.

In the present exemplary embodiment of the present invention, the gas socket 10 is further provided a pin 10c extending axially through the inside of the gas socket 10, preferably to a position just to the inner side of the seal member 10b. Just inside the gas plug 17 is peripherally provided a sealing member or seat such as an O-ring 17c against which a gas stopping ball 17c is sealingly urged by a spring 17d. Accordingly, the gas plug 17 remains closed to the passage of gas when the gas socket 10 is not engaged therewith as shown in FIG. 15A.

When the connection of the gas socket and plug 10 and 17 is being made as described above, after the tapered portion 17a passes the seal member 10b, thereby providing a seal, the pin 10c contacts the gas stopping ball 17e. As the gas socket 10 moves more rearward, the pin 10c urges the gas stopping ball 17e rearward, thereby breaking the seal between the gas stopping ball 17e and the O-ring seat 17c. Accordingly, gas is now able to pass from the gas plug 17 through to the gas socket 10.

The connection relationship between the electrical connectors 9 and 16 and the gas connectors 10 and 17 is analogous to that described above. Referring specifically to FIG. 15C, although the electrical plug 16 is completely received in the electrical socket 9 (not shown; see FIG. 4B), there is still a small gap or allowance g between the connection end of the gas socket 10 and the connection end of the gas plug 17 to accommodate wear or shifting in the electrical and gas connections. One of the advantages of this exemplary embodiment is that a dedicated external gas shut-off valve does not have to be provided on the gas piping 19.

Furthermore, by employing a gas coupler with the gas stopping mechanism as described above, when inserting or removing a gas analyzer unit 1 it is unnecessary to access a gas shut-off valve such as an electric solenoid valve, a needle valve, and the like. This not only lowers the cost of the gas analyzing apparatus but also improves the safety of operating the apparatus by eliminating possible malfunction of external valves or operator error in forgetting to close external valves.

Another exemplary embodiment of the present invention is illustrated in FIGS. 16 through 19, wherein a coupler having a plurality of independent gas connectors is provided. The couple includes a gas plug 40 mounted in the rear plate 11 of the container case 2 with, for example, a mounting screw 42, and a gas socket 41 mounted in the rear plate 8 of the main body 3 of the gas analyzer unit 1 with, for example, a mounting screw 43.

Figure 17A:
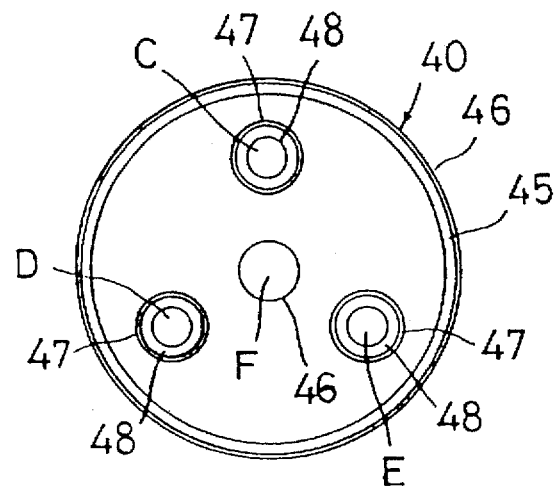
FIGS. 17A and 17B are plan views illustrating exemplary configurations of a connector according to the present invention.

With additional reference to FIG. 17A, the gas plug 40 has a large-diameter plug element 44 formed on a connection side thereof with a tapered portion 44a. A hole 46 is provided in a substantially central portion of a bottom portion 40b of the gas plug 40, serving connective purposes. The gas plug 40 has a plurality of plug connectors 47 protruding from the bottom portion 40b on the inside of the plug element 44. Each of the plug connectors 47 has a tapered portion 47a on the outer periphery thereof and a seal member 48 disposed in a groove formed near each of the tapered portions 47a, preferably in a circumferential and equally arranged relationship.

Figure 17B:
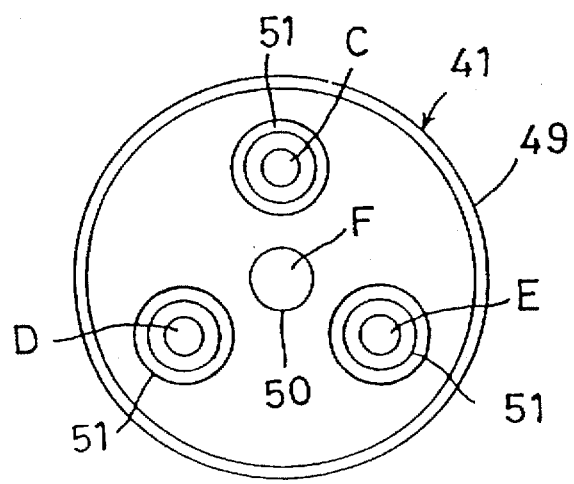

With additional reference to FIG. 17B, the gas socket 41 has a socket element 49 with a tapered portion 49a configured to be complementary for engagement with the plug element 44 with the tapered portion 44a of the gas plug 40. The gas socket 41 has a hole 50 provided in a substantially central portion of the bottom portion 49b of the socket element 49, serving connective purposes. The gas socket 41 also has a plurality of socket connectors 51 protruding from the bottom portion 49b and inside the socket element 49. Each of the socket connectors 51 has a tapered portion 51a formed on an end face thereof. The arrangement of the socket connectors 51 corresponds and is complementary to the arrangement of the plug connectors 47 of the gas plug 40.

Figure 18:
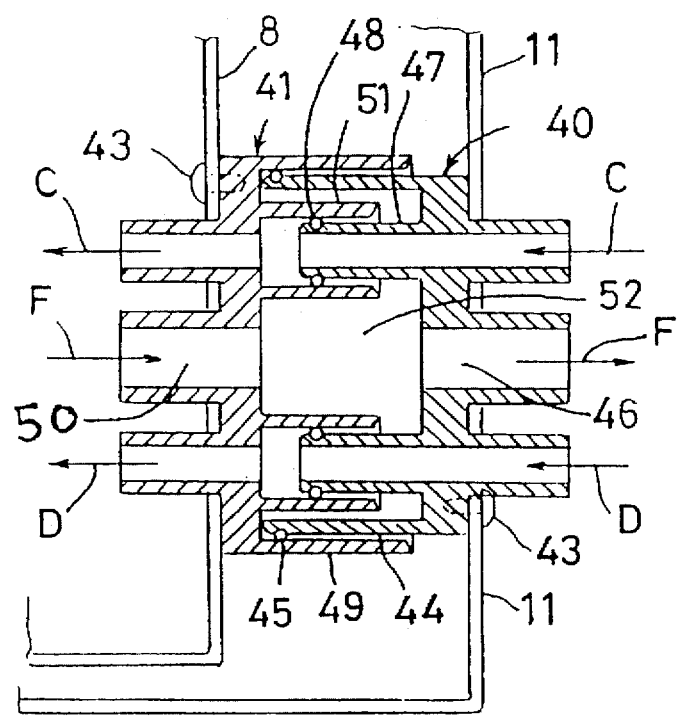
FIG. 18 is a cross-sectional view showing a connected state of the connector of FIG. 17.

With additional reference to FIG. 18, when the gas plug 40 is inserted into the gas socket 41, the space between the plug element 42 and the socket element 49 is sealed by the seal member 45 slidably and sealingly engaging with the inner periphery of the socket element 49. Similarly, the space between each of the plug connectors 47 and each of the respective socket connectors 51 is sealed by the seal member 48 slidably and sealingly engaging with the inner periphery of each of the socket connectors 51.

Three gas passages C, D, and E are formed by the respective connections between the socket connectors 51 and the plug connectors 47. A gas passage F is defined by an internal space 52 formed by the holes 46 and 50 and the plug and socket elements 44 and 49. Accordingly, a plurality of passages C, D, E, and F are formed independently, with the passage F defining an outward passage and the passages C, D, and E defining inward passages. Therefore, a plurality of gas lines may be connected to the gas plug 40, thus to the gas analyzer unit 1, simultaneously.

In the exemplary embodiment, three inward passages C, D, and E serve as gas supply lines to the gas analyzer unit 1, and the outward passage F serves as a gas discharge or exhaust line for the gas analyzer unit 1. The gas analyzer units 1 may comprise any type of gas analyzer, including non-dispersion infrared gas analyzers (NDIR), chemical luminescence gas analyzers (CLA), and hydrogen flame ionization analyzer (FID), of which the CLA has a reaction cell in a reduced pressure state. Accordingly, in the event that one of the inward passages C, D, and E develops a gas leak, the leaking gas will enter the outward passage F, will be exhausted thereby, and will not escape outside of the gas plug/socket connection. As such, the safety of the gas analyzing apparatus is greatly improved.

By providing a relatively large-diameter external coupler with an exhaust line in communication with the exhaust gas passage F, the gas coupler is provided a forced exhaust effect due to suction from the exhaust line through the gas passage F, which increases safety by preventing accidents due to leakage within the gas coupler within the space 52 defined by the sealed plug and socket elements 44 and 49. In addition, when the gas analyzer unit 1 is being removed from the container case 2, the seals between the plug connectors 47 and the socket connectors 51 are broken before the seal between the plug element 40 and the socket element 41. Accordingly, any gas which may be incoming through passages C, D, or E will enter the interior of the coupler in space 52 and will be exhausted out of the coupler through passage F, thereby preventing the leakage of gas into the rear portion of the container case 2. Therefore, safety is once again improved upon over conventional apparatus with this self-exhausting feature of the gas coupler.

Figure 19A:
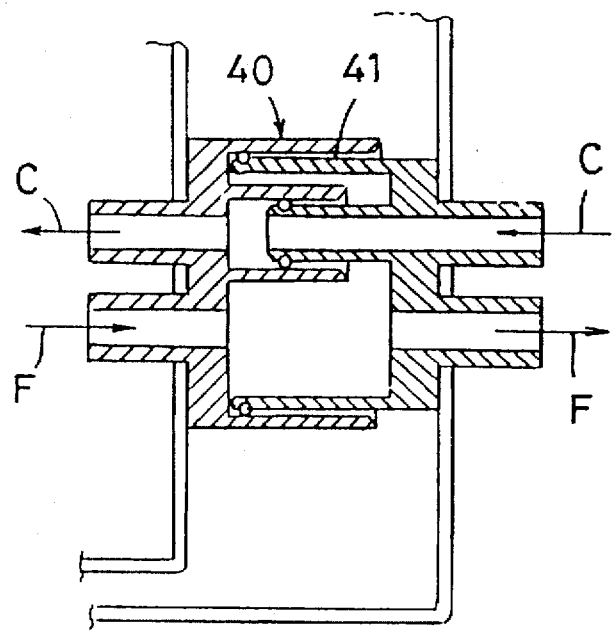
FIG. 19A is a cross-sectional view and FIG. 19B is a plan view illustrating another exemplary embodiment of a connector in accordance with the present invention.
Figure 19B:
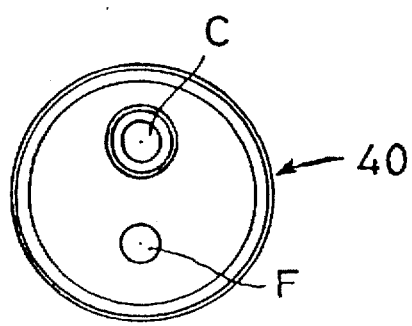

With reference to FIGS. 19A and 19B, although the exemplary embodiment described above includes a plurality of inward gas passages, the gas analyzing apparatus may comprise only a single inward gas passage C with the outward gas passage F.

Accordingly, the advantages of the gas analyzing apparatus of the present invention include frontal loading and removal of analyzer units, space-saving design from both a construction and installation point of view, electrical connector-guiding gas connectors, and the elimination of dedicated guiding mechanisms and gas shut-off valve mechanisms, which advantages either reduce the cost of manufacturing or increase the safety of operating the detachable gas analyzing apparatus.

Further, the detachable gas analyzing apparatus of the present invention advantageously maintains the small gap or allowance between the gas connectors to compensate for a change in the relative linear position, i.e., in the insert/remove direction. Therefore, the connection between the electrical connectors are made securely and safely, eliminating the chance of electrical or thermal ignition of gases and the chance of an electrical short. Also, the tolerances on the dimensions of the various connectors does not need to be as stringent with the provision of the gap, thereby lowering the cost of manufacturing the gas analyzing apparatus.

Still further, the gas analyzing apparatus according to the present invention provides additional safety features in that the gas coupler is provided an exhaust outlet for gas that may leak from individual socket and plug connectors, thereby preventing accidental ignition of gases in the apparatus or leakage of harmful gases into the installation area.

It is to be understood that the embodiments of the present invention disclosed herein are illustrative of the principles of the invention and that other modifications may be employed within the scope of the appended claims. Accordingly, the present invention is not limited to that precisely shown and described in the present specification.

What is claimed is:

1. A detachable gas analyzing apparatus comprising:

a plurality of gas analyzer units each having a rear plate provided with an electrical connector and at least one gas connector and having an engaging rail; and a container case for slidably accommodating the gas analyzer units therein in a substantially mutually parallel arrangement, the container case having a rear side provided with a plurality of electrical connectors correspondingly aligned with and complementary to the electrical connectors of the gas analyzer units, and a plurality of gas connectors correspondingly aligned with and complementary to the gas connectors of the gas analyzer units, the container case having a plurality of guides disposed in a substantially parallel manner on a bottom thereof for respectively engaging with the engaging rails of the gas analyzer units, each of the gas analyzer units being independently insertable into and removable from the container case.

2. The detachable gas analyzing apparatus as set forth in claim 1 wherein each of the gas analyzer units includes a front plate, and the container case includes a bottom plate with a plurality of grooves formed in a front portion thereof, the gas analyzing apparatus further comprising:

a plurality of screws, each screw being rotatably mounted in a lower portion of the front plate of one of the gas analyzer units;

a plurality of nut members, each nut member being threadingly engaged with one of the screws and having a first abutting portion and a second abutting portion, the first abutting portion of each nut member for engaging with one of the grooves to prevent the nut member from rotating in a first direction, and the second abutting portion of the nut member for engaging with the bottom plate of the container case to prevent the nut member from rotating in a second direction; and a plurality of spring members, each spring member being disposed between one of the nut members and the front plate of the gas analyzer unit, the spring member urging the nut member to be responsively rotatable with the screw.

3. The detachable gas analyzing apparatus as set forth in claim 2 wherein each spring member comprises a coil spring disposed around the screw.

4. The detachable gas analyzing apparatus as set forth in claim 2 wherein each spring member comprises a plate spring, the plate spring including:

a planar portion abutting the nut member;

a hole formed in the planar portion through which the screw is received; and leg portions extending angularly from the planar portion toward the front plate of the gas analyzer unit.

5. The detachable gas analyzing apparatus as set forth in claim 1 further comprising:

a plurality of abutting portions, each abutting portion being mounted to the front side of one of the gas analyzer units; and a plurality of clamping elements, each clamping element being rotatably mounted to a front side of the container case and being rotatable to contact one of the abutting portions to urge the gas analyzer unit rearward into the container case.

6. The detachable gas analyzing apparatus as set forth in claim 1 wherein:

the at least one gas connector of each of the gas analyzer units has a tapered portion formed thereon; and each gas connector of the container case has a tapered portion formed thereon complementary to the tapered portion of the gas connectors of the gas analyzer units;

the gas connectors with the tapered portions self-aligning as the gas analyzer unit is being inserted into the container case.

7. The detachable gas analyzing apparatus as set forth in claim 1 wherein:

a seal is made in the gas connectors prior to a connection being made in the electrical connectors; and a gap remains between each gas connector of the gas analyzer units and each gas connector of the container case when the electrical connectors are completely connected.

8. The detachable gas analyzing apparatus as set forth in claim 6 wherein each gas connector of the gas analyzer units is a gas socket, and each gas connector of the container case is a gas plug, the gas plug being slidably receivable in the gas socket and further comprising a gas stop mechanism provided in the gas connectors for stopping the flow of gas from the gas plug to the gas socket when disconnected, the gas stop mechanism comprising:

a seat defined by the inner periphery of the gas plug;

a gas stopping ball disposed within the gas plug;

a spring disposed within the gas plug for urging the gas stopping ball against the seat to seal the gas plug when the gas plug is disconnected from the gas socket; and a pin disposed centrally within the gas socket for urging the gas stopping ball away from the seat when the gas plug is inserted into gas socket.

9. The detachable gas analyzing apparatus as set forth in claim 7 wherein each gas connector of the gas analyzer units is a gas socket, and each as connector of the container case is a gas plug, the gas plug being slidably receivable in the gas socket and further comprising a gas stop mechanism provided in the gas connectors for stopping the flow of gas from the gas plug to the gas socket when disconnected, the gas stop mechanism comprising:

- a seat defined by the inner periphery of the gas plug;
- a gas stopping ball disposed within the gas plug;
- a spring disposed within the gas plug for urging the gas stopping ball against the seat to seal the gas plug when the gas plug is disconnected from the gas socket; and
- a pin disposed centrally within the gas socket for urging the gas stopping ball away from the seat when the gas plug is inserted into the gas socket.

10. The detachable gas analyzing apparatus as set forth in claim 6 wherein each gas connector of the gas analyzer units is a gas socket, and each gas connector of the container case is a gas plug, the gas plug being slidably receivable in the gas socket;

- the gas plug including at least one plug connector having a seal member on the outer periphery thereof, a plug element extending circumferentially around the gas plug and having a seal member disposed on the outer periphery thereof, and a hole formed therethrough;
- the gas socket including at least one socket connector correspondingly aligned with and complementary to the at least one plug connector, a socket element extending circumferentially around the gas socket, and a hole formed therethrough;
- seals being formed when the gas plug is connected with the gas socket between the at least one plug connector and the at least one socket connector and between the plug element and the socket element; and
- gas passages being formed when the gas plug is connected with the gas socket by the connection of the at least one plug connector with the at least one socket connector and by the communication of the respective holes of the gas socket and the gas plug.

11. The detachable gas analyzing apparatus as set forth in claim 7 wherein each gas connector of the gas analyzer units is a gas socket, and each gas connector of the container case is a gas plug, the gas plug being slidably receivable in the gas socket;

- the gas plug including at least one plug connector having a seal member on the outer periphery thereof, a plug element extending circumferentially around the gas plug and having a seal member disposed on the outer periphery thereof, and a hole formed therethrough;
- the gas socket including at least one socket connector correspondingly aligned with and complementary to the at least one plug connector, a socket element extending circumferentially around the gas socket, and a hole formed therethrough;
- seals being formed when the gas plug is connected with the gas socket between the at least one plug connector and the at least one socket connector and between the plug element and the socket element; and
- gas passages being formed when the gas plug is connected with the gas socket by the connection of the at least one plug connector with the at least one socket connector and by the communication of the respective holes of the gas socket and the gas plug.

12. The detachable gas analyzing apparatus as set forth in claim 10 wherein an exhaust line is in communication with the gas passage formed by the respective holes of the gas socket and the gas plug;

whereby gas leaking within the plug and socket elements will be exhausted out of the coupler through the exhaust line.

13. The detachable gas analyzing apparatus as set forth in claim 11 wherein an exhaust line is in communication with the gas passage formed by the respective holes of the gas socket and the gas plug;

whereby gas leaking within the plug and socket elements may be exhausted out of the coupler through the exhaust line.

* * * * *

UNITED STATES PATENT AND TRADEMARK OFFICE
CERTIFICATE OF CORRECTION

PATENT NO. : 5,746,976
DATED : May 5, 1998
INVENTOR(S) : Shinsaku Yamada, Hideki Ohashi, Sumio Shimizu, Takao Imaki It is certified that error appears in the above-indentified patent and that said Letters Patent is hereby corrected as shown below:

Column 15, line 1, between the words "each" and "connector" delete the word "as" and insert the word --gas--.

Signed and Sealed this

Twenty-first Day of July, 1998

*Attest:*

BRUCE LEHMAN

*Attesting Officer*  *Commissioner of Patents and Trademarks*